(12) United States Patent
Van den Berg et al.

(10) Patent No.: US 7,673,991 B2
(45) Date of Patent: Mar. 9, 2010

(54) METHOD AND DEVICE FOR MEASURING RETINAL STRAY LIGHT

(75) Inventors: Thomas Joannes Theodorus Paschalis Van den Berg, Abcoude (NL); Joris Eduard Coppens, Amsterdam (NL)

(73) Assignee: Koninklijke Nederlandse Akademie van Wetenschappen, Amsterdam (NL)

( * ) Notice: Subject to any disclaimer, the term of this patent is extended or adjusted under 35 U.S.C. 154(b) by 624 days.

(21) Appl. No.: 10/570,676

(22) PCT Filed: Aug. 12, 2004

(86) PCT No.: PCT/NL2004/000569

§ 371 (c)(1),
(2), (4) Date: Apr. 23, 2007

(87) PCT Pub. No.: WO2005/023103

PCT Pub. Date: Mar. 17, 2005

(65) Prior Publication Data

US 2007/0273833 A1    Nov. 29, 2007

(30) Foreign Application Priority Data

Sep. 5, 2003    (NL) .................................... 1024232

(51) Int. Cl.
*A61B 3/10* (2006.01)
(52) U.S. Cl. ................... 351/221; 351/205; 351/210
(58) Field of Classification Search ................. 351/221, 351/237, 246, 205, 210
See application file for complete search history.

(56) References Cited

U.S. PATENT DOCUMENTS

| 4,854,692 | A |   | 8/1989  | Kobayashi |
|-----------|---|---|---------|-----------|
| 5,284,149 | A |   | 2/1994  | Dhadwal et al. |
| 5,632,282 | A | * | 5/1997  | Hay et al. .................... 600/558 |
| 5,671,039 | A |   | 9/1997  | Grolman |
| 6,141,092 | A | * | 10/2000 | Kim ........................... 356/214 |
| 2003/0038921 | A1 |  | 2/2003 | Neal et al. |

FOREIGN PATENT DOCUMENTS

| EP | 0366421 A | 5/1990 |
| EP | 0724858 A | 8/1996 |

OTHER PUBLICATIONS

T.J.T.P. Van Den Berg: "Clinical assessment of intraocular stray light" *Applied Optics*, vol. 31, No. 19, Jul. 1, 1992, pp. 3694-3696.

* cited by examiner

*Primary Examiner*—Joseph Martinez
*Assistant Examiner*—James R Greece
(74) *Attorney, Agent, or Firm*—Morgan, Lewis & Bockius LLP

(57) ABSTRACT

The present invention provides a method and device of measuring the retinal stray light in the eye of a subject, comprising presenting to the subject a flickering stray light from a stray light source; presenting to the subject compensation light so as to undercompensate said part of the flickering stray; presenting to the subject compensation light, the compensation light flickering with a modulation depth so as to eventually overcompensate the flickering light being imaged on the retina; and determining from the results of a sequence of comparisons using different parameter values between the resulting retinal light flickering as perceived by the subject for the undercompensated test area and the eventually overcompensated test area a stray light parameter.

36 Claims, 8 Drawing Sheets

METHOD AND DEVICE FOR MEASURING RETINAL STRAY LIGHT

CROSS-REFERENCE TO RELATED APPLICATION

This Application is a Section 371 National Stage Application of International Application No. PCT/NL2004/000569, filed 12 Aug. 2004 and published as WO 2005/023103 A1 on 07 Mar. 2005, which claims the priority from the Netherlands patent application 1024232, filed 5 Sep. 2003, the subject matter of which are hereby incorporated by reference in their entirety.

The present invention relates to a method and device for measuring retinal stray light in the eye.

One of the factors relevant to the optical clarity of the eye is the amount of forward light scatter in the optical media, especially the crystalline lens, of the eye. Light scatter causes a veil of false light over the retina, the so-called retinal stray light. This reduces contrast of the image projected on the retina by the same optical refracting elements of the eye. Increased retinal stray light causes the first complaints when cataract develops. It is the cause of glare during driving at night and the first reason to stop driving. The amount of retinal stray light can be used as a criterion for the surgical procedure of cataract extraction, or as criterion for driver licensing. Also corneal and other pathologies may contribute to the amount of light scatter in an eye. It is therefore important to have a method and a device at one's disposal for accurately measuring the total amount of forward light scatter in an eye by measuring the retinal stray light level, the method at least being suitable for clinical use as well as driver licensing.

Intraocular light scatter is the phenomenon that part of the light reaching the retina does not partake in normal image formation. Rays originating from a certain point in space are converged by the refracting elements of the eye to the focal area in the eye, the retina. Some of the rays are dispersed to other areas by optical imperfections of the eye. This occurs especially in pathological states, such as cataract, corneal dystrophy, floating particles in the chambers, etc. These dispersed rays are distributed all over the retina, but with decreasing densities at distances further away from the original focal area. Through this effect, the retinal light distribution in any visual environment is composed of two parts: the image of the external world based on the focused rays, superimposed upon a more or less homogeneously distributed background, caused by the dispersed rays. As a result contrast is lost in the image of interest. The severity of this contrast loss depends on the illuminance ratio between background and image. The extreme situation is represented by the classical glare condition: strong light somewhere in the visual field while a weakly lit object has to be observed. Depending on the angular distance between glare source and object this situation can lead to complete blinding. The typical situation is blinding by oncoming traffic at night.

The importance of intraocular light scatter has long been recognized, and several techniques have been proposed for assessment of its importance in individual subjects. As a rule these techniques do not assess retinal stray light or light scatter itself, but some derived effect. For instance, an apparatus has been developed for testing the threshold intensity for a Landolt C target in the presence of a glare source. Also glare testers have been developed that simulate more or less a traffic situation. One of the problems associated with the known indirect techniques is that the results are highly unreliable. The existing indirect glare testing techniques provide only indirect information from which the amount of scatter must be deduced on the basis of sometimes complicated theoretical assumptions.

U.S. Pat. No. 5,671,039 discloses a glare tester for testing visual acuity. The tester includes an annular ring provided with a plurality of light sources mounted in recesses to direct light towards a test axis and a surface to reflect the light from the light sources towards the patient's eye. The doctor turns on the light sources at a low level and observes the change in the patient's acuity when the patient tries to read a projected test symbol or wall chart. Additionally the test may be conducted by briefly flashing the light sources or an additional light source. Results of the glare test are obtained by determining the time required for the patient's eye to identify the symbol presented to the patient. Since also this glare tester assesses a derived effect of the intraocular light scatter rendering the results of the test highly unreliable.

In the article "Clinical Assessment of intraocular stray light", Applied Optics, Vol. 31, No. 19, 1 Jul. 1992 the inventor of the present application describes the so-called direct compensation method for directly measuring the amount of retinal stray light for each angular distance tested. Nowadays the direct compensation method is considered by experts in the field as the standard for intraocular light scatter measurement. The direct compensation method works as follows. A bright light source at a certain angular distance from a test field is presented flickering. Due to intraocular scatter, a part of the light from the bright stray light source will be imaged on the retina at the location of the test field, inducing a weak flicker in the test field. The amount of flickering stray light in the test field is directly related to the amount of scattering of the eye media. To measure the amount of stray light a variable, relatively weak, compensation light is presented in the test field. This compensation light flickers in counter-phase with the bright stray light source. By adjusting of the amount of compensation light (i.e. by changing the modulation depth or amplitude of the compensation light in the test field, cf. FIG. 5) the flicker perception in the test field can be extinguished. In this way the modulation caused by scattering from the glare source is directly compensated. The point of direct compensation is the minimum of a generally V-shaped curve (cf. FIG. 5) illustrating the course of the intensity of the physical flicker at the retina—and thus the subjective flicker percept—as a function of the intensity of the compensation light.

Although a stray light meter based on the direct compensation method is considered to be suitable for clinical assessment of intraocular stray light, it is not very well suited for routine clinical use in the hands of non-experts. Perception of the weak flicker in the test field appears to be difficult for untrained subjects, especially in the presence of the strong flicker of the stray light source. The difficulty for the subject to make a precise setting frustrates its use for routine purposes. Usually visual tests are based on what subjects do see. In the direct compensation method the opposite is the case: an adjustment has to be made to make a flicker perception disappear. Furthermore the continuous flickering of the stray light source is clearly very disturbing in making that adjustment. Many normal subjects are not used to making such precise adjustments, needed for the direct compensation method. Accuracy of the measurement is dependent on the proper explanation of the test and the best adjustment strategy. As a result the direct compensation method is less suitable for routine use.

It is therefore an object of the present invention to provide a method and device for measuring retinal stray light wherein the drawbacks of the existing methods and devices in general and the method and device of direct compensation in particular are obviated.

According to a first aspect of the invention this object is achieved in a method of measuring the retinal stray light in the eye of a subject, comprising:

presenting to the subject a flickering stray light from a stray light source positioned at a predefined angular distance from a test area, a part of the flickering stray light being imaged on the retina at a location corresponding to the location of the test area;

presenting to the subject compensation light from a compensation light source arranged at a position in the test area, the parameters of the compensation light being set so as to immediately or eventually undercompensate said part of the flickering stray light being imaged on the retina at the location corresponding to the location of the test area;

presenting to the subject compensation light from a compensation light source arranged at a position in the test area, the parameters of the compensation light being set so as to immediately or eventually overcompensate said part of the flickering light being imaged on the retina at the location corresponding to the location of the test area;

receiving an input signal representative of the result of a comparison between the resulting retinal light flickering as perceived by the subject for the undercompensated test area and the resulting retinal flicker intensity for the overcompensated test area;

varying the value(s) of one or more of said parameters defining one or more of the stray light source light and the compensation light source light;

repeating the above steps for different parameter values;

determining, using the received input signals and the corresponding parameter values of the stray light source and the compensation light sources, those parameter values wherein the perceived retinal light intensities of the undercompensated and overcompensated test area are substantially equal;

calculating from the determined parameter values a stray light parameter representative of the retinal stray light induced by the stray light source.

Instead of compensating the induced flicker in the test area until no flickering in the test area can be observed, the flicker in the test area is over- and/or under compensated, such that a flicker is still perceived. It is important to stress that the patch of retina where the test areas are projected, not only receives light from the test areas themselves, but also light from the stray light source scattered inside the eye. These flickering lights of either test area and the stray light source sum up at the retina. The retina does not "know" that the light it receives comes from different sources. The two flickering lights combine to a new flickering light, depending on the intensity ratio between the two lights. This new flicker is compared to the amount of flicker in the other test field, originating from the over- or under compensation of the other test area and the stray light source. The result of the comparison (stronger, weaker, the same) provides a good estimate for the retinal stray light induced in the eye.

In a preferred embodiment the method comprises, after having received the input signal, the steps of varying the modulation depth of the light from the stray light source after having received the input signal; and repeating the presenting steps and receiving step using the varied modulation depth of the light from the stray light source until that modulation depth of the stray light source is determined wherein the perceived retinal light intensities of the undercompensated and overcompensated test area are substantially equal. Preferably the stray light starts with relatively low luminance levels, gradually becoming brighter. By repeating the comparisons for different modulation depths of the stray light emitted by the stray light source a better estimate of the retinal stray light may be achieved.

In another preferred embodiment the method comprises, after having received the input signal, the steps of varying the modulation depth of the compensation light for at least one of the undercompensated and overcompensated test areas; and repeating the presenting steps and receiving step using at least one varied modulation depth until at least one modulation depth is determined wherein the perceived retinal light intensities of the undercompensated and overcompensated test area are substantially equal. In this embodiment the periphery light from the surroundings of the stray light source preferably has a luminance substantially equal to the luminance of the stray light source. Preferably the luminance is substantially equal to the average luminance or maximum luminance of the stray light source.

In some preferred embodiments the first en second compensation lights are presented consecutively, preferably in one test area.

In other preferred embodiments, however, the first and second compensation lights are presented simultaneously. In these embodiments the test area preferably comprises at least a first and a second test field being spatially separated, a first compensation light source being arranged at the position of the first test field and a second compensation light source being arranged at the position of the second test field.

In a further preferred embodiment the method comprises, after having received the input signal, the steps of varying the summed modulation depth of the compensation light of the undercompensated test field and the overcompensated test field, while keeping a constant difference between the modulation depths of the undercompensated and overcompensated test fields; and repeating the presenting steps and receiving step using the varied summed modulation depth until the modulation depth is determined wherein the perceived retinal light intensities of the undercompensated and overcompensated test area are substantially equal.

In a further preferred embodiment an offset in either the undercompensation or overcompensation test field is added, the offset depending on the amount of under- and overcompensation for a particular stimulus. This is to ensure that the subject gets no clues to detect a difference between the two test fields, other than a difference in the amount of flickering.

In a further preferred embodiment the average luminance of the undercompensated test field is set so as to correspond with the average luminance of the overcompensated test field presented at the same time.

In a further preferred embodiment the method comprises the step of presenting compensation light in one of the test fields without presenting light from the stray light source so as to determine the detection threshold of flickering light of the subject. In a still further preferred embodiment the method comprises the step of presenting compensation light in both test fields without presenting light from the stray light source so as to determine the discrimination threshold of flickering light of the subject. The method then preferably comprises the steps of:

presenting compensation light of varying modulation depth differences in the test fields without presenting light from the stray light source; and determining the value of the minimum modulation depth difference that can be sensed by the subject.

In a further preferred embodiment the method comprises:
determining a first estimate of the stray light parameter by using the method of varying the light from the stray light source;
determining a second estimate of the stray light parameter by using the method of varying the modulation depth of at least one of the test fields, wherein the modulation depths presented are based on the first estimate of the stray light parameter.

In a further preferred embodiment the stray light source presents flickering light at a maximum intensity.

In a further preferred embodiment a high intensity ring shaped light source surrounding the test area is provided for isolating the test area from the surroundings.

In a further preferred embodiment the test fields and/or the stray light source are presented with different colours in order to determine the stray light parameter in dependence of the wavelength of the stray light.

In most case the method will be applied to one eye at a time (monocular use). However, in a further preferred embodiment the retinal stray light in both eyes of a subject is determined simultaneously (binocular use).

In a further preferred embodiment an image is presented between consecutive presentations of stray light and compensation light. In a preferred embodiment the image has an average luminance corresponding to that of the average luminance during said presentations.

In a further preferred embodiment the test area is provided with blurred edges. This is done in order to reduce the effect of Mach bands In a further preferred embodiment variable offsets in the test fields of the test are provided. Therefore the Brücke-Bartley effect can be taken into account. This is the effect that the perceived luminance of a constant signal is not equal to the perceived luminance of a flicker signal with the same average luminance.

In a further preferred embodiment the undercompensation and overcompensation of the test fields are modulated spatially, preferably with a spatial modulation of about 2-4 Cycl/deg.

In a further preferred embodiment the light from the stray light source is aimed at the blind spot in the eye.

According to a second aspect the object of the invention is achieved in a device for measuring the optical clarity of the eye of a subject, comprising:
first display means for presenting to the subject a flickering stray light from a stray light source positioned at a predefined angular distance from a test area, a part of the flickering stray light being imaged on the retina at a location corresponding to the location of the test area;
second display means for presenting to the subject compensation light from a compensation light source arranged at a position in the test area, the parameters of the compensation light being set so as to immediately or eventually undercompensate said part of the flickering stray light being imaged on the retina at the location corresponding to the location of the test area;
third display means for presenting to the subject compensation light from a compensation light source arranged at a position in the test area, the parameters of the compensation light being set so as to immediately or eventually overcompensate said part of the flickering light being imaged on the retina at the location corresponding to the location of the test area;
input means for receiving an input signal representative of the result of a comparison between the resulting retinal flicker intensity as perceived by the subject for the undercompensated stray light and the resulting retinal flicker intensity for the overcompensated stray light;
first processing means for varying the value or values of one or more of the parameters defining at least one of the light from the first, second and third display means;
second processing means for determining the parameter values of the light from the stray light source, the undercompensated test area and the overcompensated test area wherein the perceived retinal light intensities of the undercompensated and overcompensated test area are substantially equal;
third processing means for calculating from the determined parameter values a stray light parameter representative of the retinal stray light induced by the stray light source.

In preferred embodiments the display means comprise a Cathode Ray Tube (CRT) or a Digital Light Processing (DLP) device.

Further advantages, features and details of the present invention will be elucidated on the basis of the description of preferred embodiments thereof. Reference is made in the description to figures, in which.

Although the present method for measuring forward light scatter in an eye will be described in connection with various preferred embodiments, there is no intent to limit it to that embodiments. On the contrary, the intent is to cover all alternatives, modifications and equivalences included within the spirit and the scope of the method as defined by the appended claims.

Figure 1:
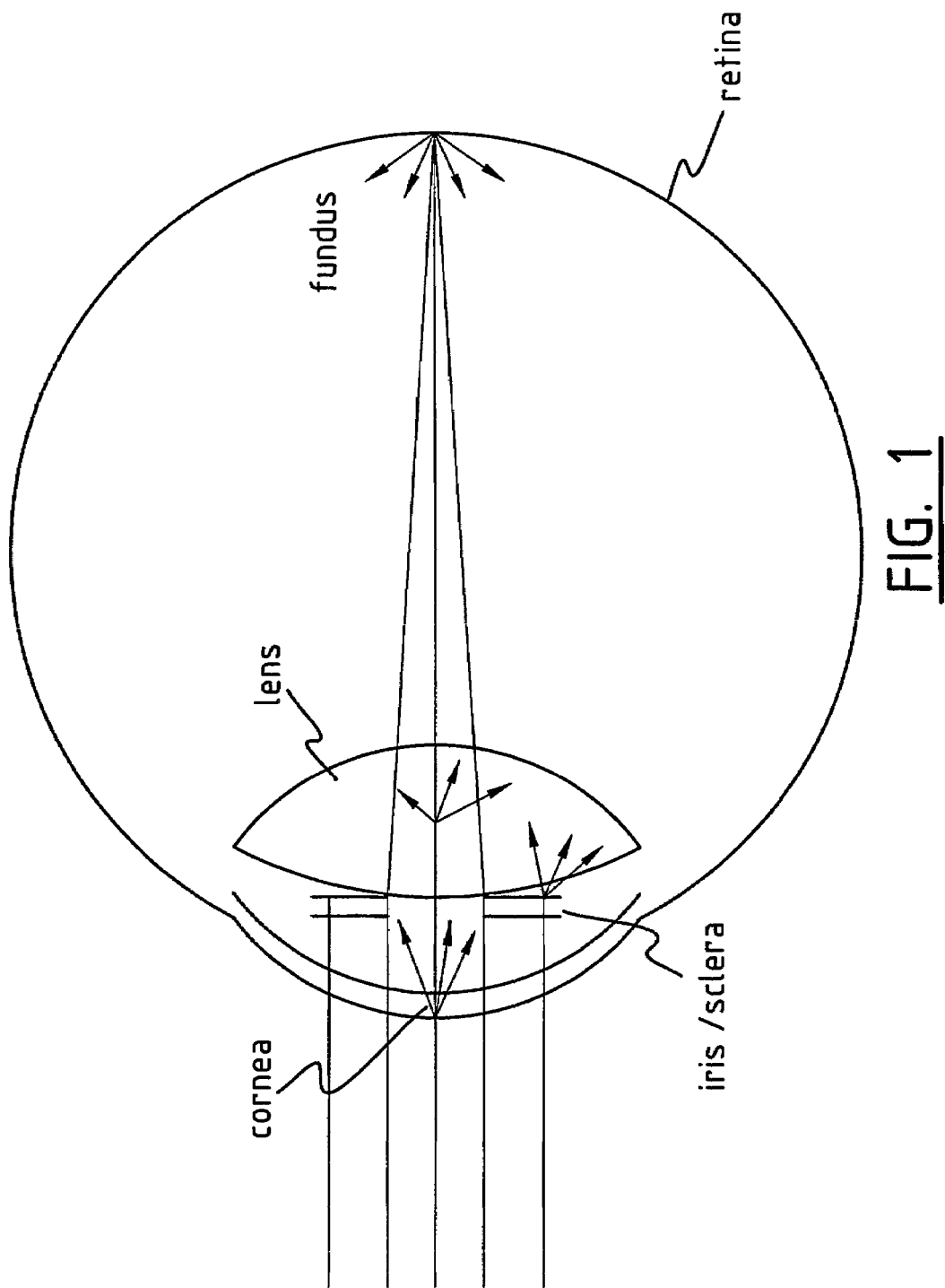
FIG. 1 represents a schematic cross-section of the human eye, wherein the four primary sources of stray light are shown.

Because of their biological making the optical media in the eye contain optical imperfections resulting, in an optical sense, in non-ideal behaviour of the eye. The imperfections in the eye give rise to various aberrations, one of them being the occurrence of stray light. An overview of four important sources of stray light is given in FIG. 1. For example, cornea and lens contain refractive structures such as cell membranes, collagen fibres and proteins that have no perfect crystalline ordering. Also the boundaries of cornea and lens are somewhat irregular. This results in a considerable light scatter in the eye. Moreover the eye wall (i.e. the iris and sclera-choroid-RPE) is not perfectly light tight. Also a part of the light reaching the fundus of the eye is reflected. The contributions of these effects to the total light scattering in the eye depend amongst others on the age and pigmentation (skin colour and eye colour) of the person. As mentioned earlier the amount of stray light is important in determining the quality of vision.

The light that is scattered due to the different stray light sources is not uniformly distributed across the entire retina. There is a higher density near the spot on the retina where the images are formed. The distribution of intensity on the retina caused by a point shaped light source is called the point spread function (PSF). The shape of the PSF is directly related to the amount of stray light. If the intensity is higher in the centre where the image is formed, less light is received on other parts of the retina. To determine the shape of the PSF the distribution of the intensity of the perceived light must be measured.

Figure 3:
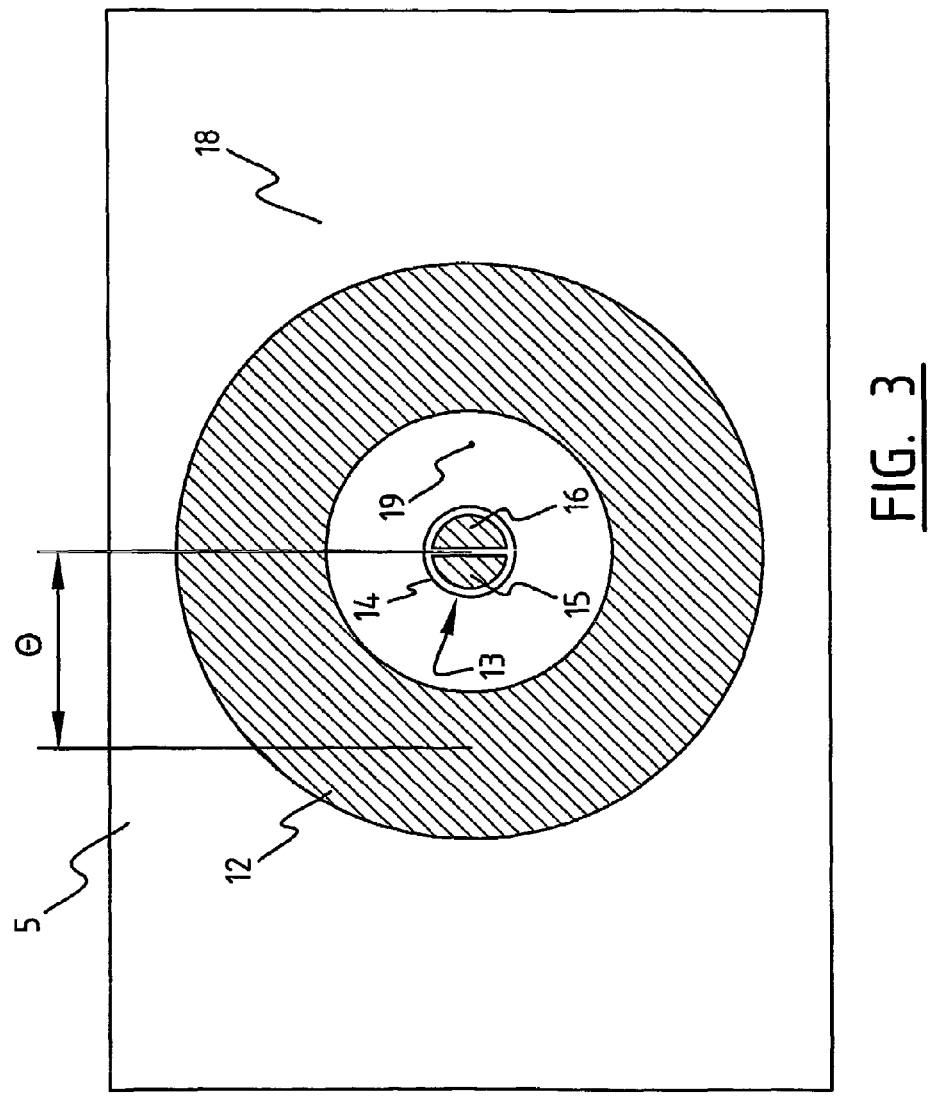
FIG. 3 shows a front view of a preferred embodiment of the stimulus field layout represented on the display device.
Figure 4:
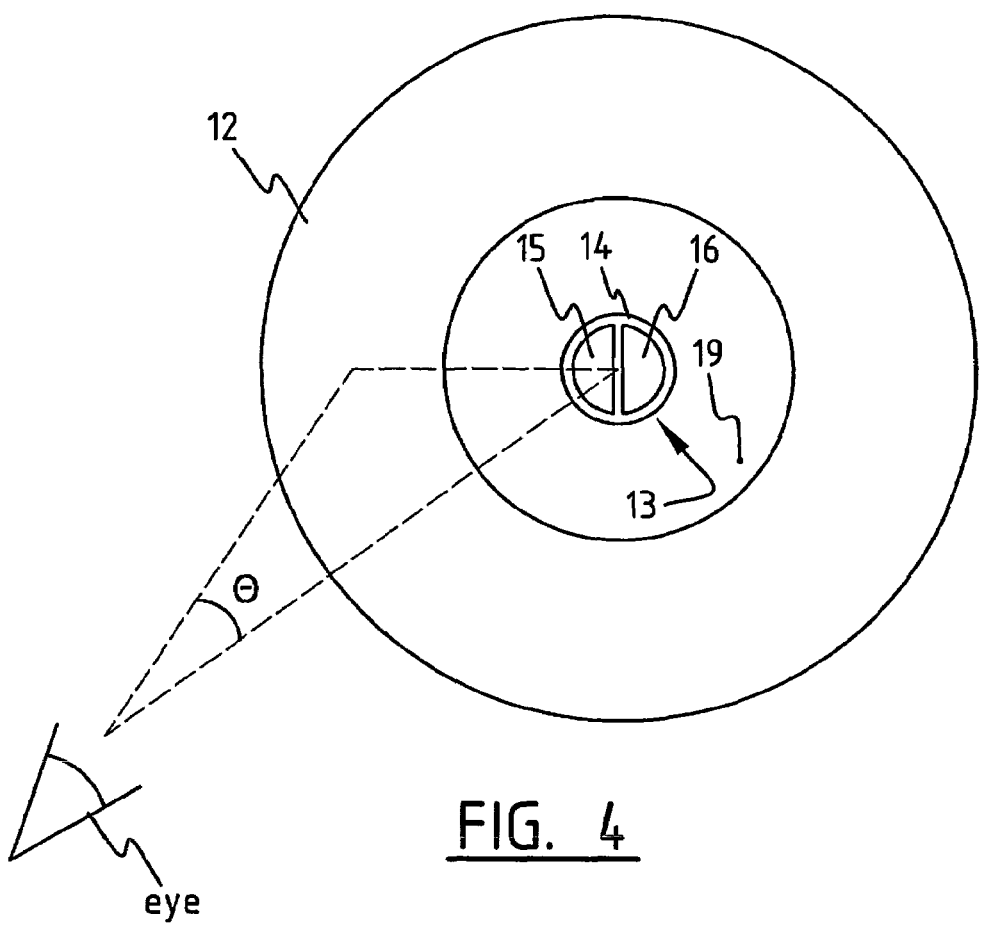
FIG. 4 shows a perspective view of the geometrical arrangement of the preferred embodiment of the stimulus field layout represented on the display device as shown in FIG. 3.

Stray light may be defined by means of the equivalent luminance ($L_{eq}$), which is defined as the background luminance (in $cd/m^2$) that has the same visual effect (e.g. the same adaptive effect on visual sensitivity) as the veil caused by respective stray light sources at some angular distance θ (FIG. 3 or FIG. 4). For normalization purposes the equivalent luminance is divided by the illuminance $E_{gl}$ (in $lm/m^2$) in the plane of the pupil originating from the stray light source. This normalized value is the Point Spread Function $PSF(\theta)=L_{eq}/E_{gl}$. The PSF is a function of the angle between glare source and test field. For angles more than 1 degree this function is approximately proportional to $1/\theta^2$ (Stiles-Holladay approximation). To better indicate deviations in angular behaviour from the Stiles-Holladay approximation of the Point Spread Function the so-called stray light parameter (s) is introduced as $s(\theta)=\theta^2 L_{eq}/E_{gl}$. One of the benefits of this definition of the stray light parameter is that it is only very weakly dependent on the distance between eye and the stray light source (for example a display device of a stray light meter). A more elaborate discussion about the definition of the stray light parameter s is given in the article "Analysis of intraocular stray light, especially in relation to age", T. J. T. P. van den Berg, Optometry and vision science, 1995, Vol. 72, No. 2, pages 52-59, the content of which is incorporated herein by reference.

Figure 2:
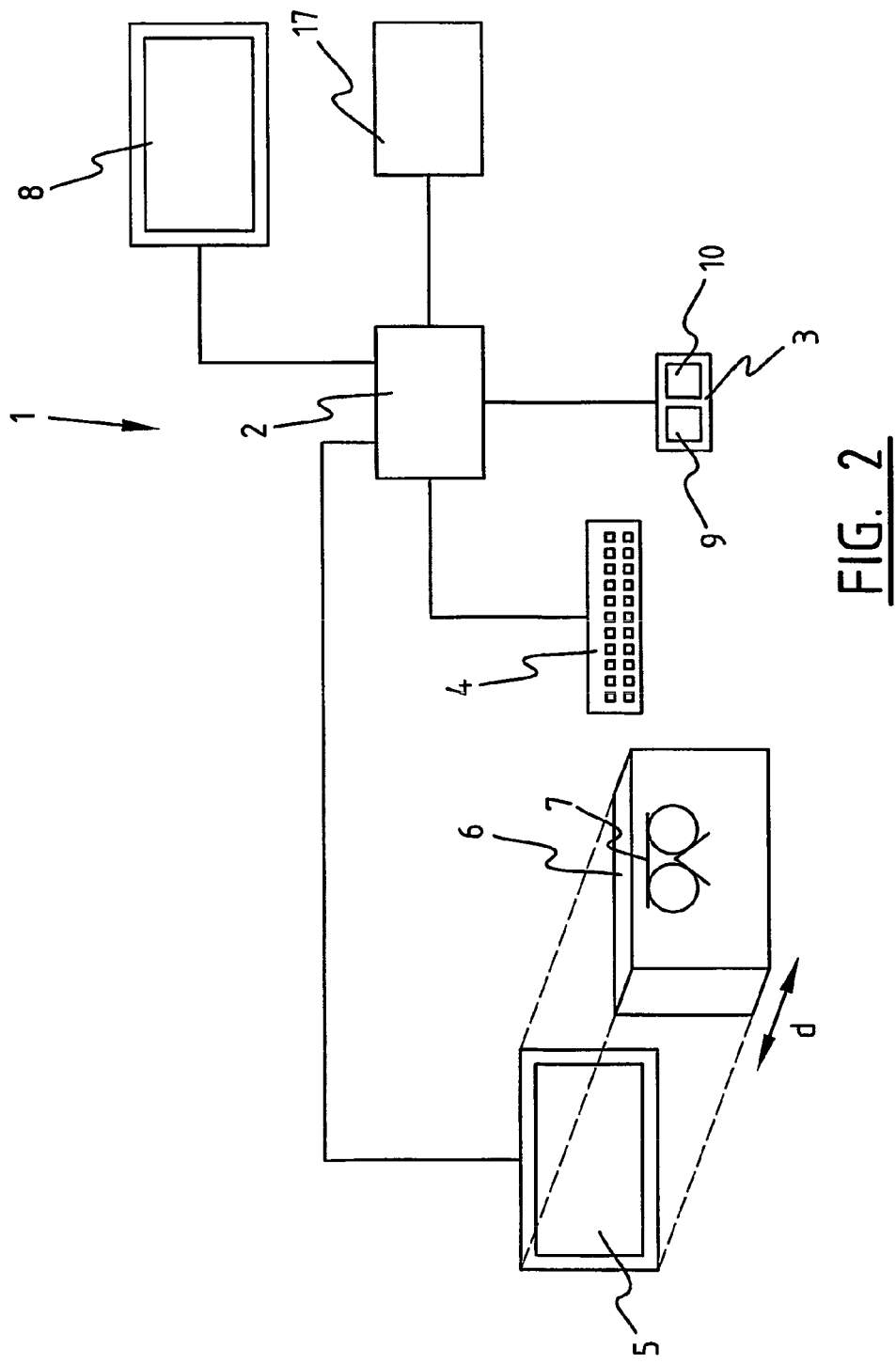
FIG. 2 shows a schematic representation of a stray light measuring device according to a first embodiment of the present invention.

In order to provide a measure for the stray light induced in the eye by a stray light source a measuring device is provided, a first preferred embodiment of which is shown in FIG. 2. FIG. 2 shows a computer 1 including a processing unit 2, a storage means 17, for example a hard disk or a memory, a first input terminal 3 for the test subject and a second input terminal 4 for the operator and a display 5 for presentation of stimuli to a subject. The display is provided with an enclosure 6 for the purpose of shielding the display 5 from environmental light. The enclosure 6 has a headrest 7 in order to ensure a constant distance between eye and display 5.

In the embodiment shown in FIG. 2 the stimuli are presented on a CRT or equivalent display device. The stimuli are generated by a processing unit and presented on the display 5. Also a second display device 8 is available for the operator. The first input terminal comprises two response buttons 9,10 for collecting responses from the subject to the stimuli provided. These buttons are connected to the personal computer via a suitable interface (for example a Universal Serial Bus interface). The responses can thus be sent to the processing unit. Based on the received responses from the subject and the stimuli shown on the display the processing unit is able to determine the stray light parameter s, as will be described hereafter.

First of all calibration of the measuring device 1 is needed. Because the luminance (i.e. the physical measure of the amount of light an object sends out) of a display device, for example a CRT, is not linear with the luminance RGB-code (which is a number between 0 and 255 for an 8 bit DAC) used by the computer to define the colour and brightness of each pixel, calibration of the display device is necessary.

Calibration of the luminance of the stimulus display to luminance code is done with a photodiode. A photodiode suitable for this purpose is a UDT PIN-10AP, manufactured by United Detector Technology Inc. Santa Monica, Calif., U.S.A. The photodiode is arranged close to or on the display device so as to avoid external influences, for example ambient light, as much as possible. The luminance of the display device is measured by integrating the current from the photodiode during one frame of the display device. An integrator suitable for this purpose is the TI IVC102, manufactured by Texas Instruments (Burr Brown). The charge, accumulated during a frame, is measured and converted after each frame to a 16-bit digital code. The corresponding digital luminance code is transferred to the personal computer 1 via the USB interface. For this purpose a parallel interface may be used. During the calibration procedure stimuli identical to those used during testing are displayed in order to ensure identical conditions during calibration and measurement of an eye. This way, shortcomings of the display device, such as internal scatter, are implicitly accounted for.

In order to be able to create stimuli with more than 256 intensity values (maximum achievable with an 8 bit DAC (Digital to Analog Converter) in the computer's graphics card), noise is added to the luminance code of each pixel independently. It is of importance to create more than 256 intensity values, because the straylight corresponds to about 1% of the maximal luminance of the display in case of young subjects with normal levels of stray light.

The calibration is based on the following consideration. In one of the preferred embodiments (as for example is shown in FIG. 3) the stray light source is an annulus. The fraction, f, of light from the annulus that scatters to the central test field, for an eye with s=1, can be calculated as follows:

$$f = 2\pi \left(\frac{\pi}{180}\right)^2 \int_{\theta_1}^{\theta_2} \frac{1}{\theta} d\theta,$$

where $\theta_1$ is the inner radius of the annulus, and $\theta_2$ the outer radius of the annulus. Preferably the ratio of outer and inner radii is 2, resulting in a fraction $$f = 2\frac{\pi^3}{180^2}\ln(2) \approx 0.0013.$$

For ease of calculation this formula can be approximated to a high degree of accuracy as follows. If an annulus of $\theta_1$ degrees to $\theta_2$ degrees of luminance c [$cd/m^2$] is presented, then in the center of that annulus the (equivalent) luminance $L_{eq}$ due to straylight on the retina is equal to $$L_{eq}=0.0044 \cdot s \cdot {}^{10}\log(\theta_2/\theta_1) \cdot c \ (cd/m^2)$$

Hence, if the point of symmetry between under- and over-compensation (the prior "direct compensation" point) is found to be at $L_{eq}[cd/m^2]$, then the straylight parameter s for that subject at that angular distance (effectively equal to the geometrical mean $\sqrt{(\theta_2 \cdot \theta_1)}$) is:

$$s = L_{eq}/0.0044 \cdot {}^{10}\log(\theta_2/\theta_1) \cdot c = f/0.0044 \cdot {}^{10}\log(\theta_2/\theta_1)$$

in this formula the fraction $f = L_{eq}/c$ appears. This fraction $f = L_{eq}/c$ is the ratio between the compensation luminance needed in the center and the luminance of the annulus. Hence, the luminance in the centre and the luminance in the annulus need to be calibrated. It suffices to establish what fraction f of the luminance in the center originates from the luminance in the annulus. In fact, each value of the fraction f can directly be translated in the straylight parameter s according to this formula.

Figure 5:
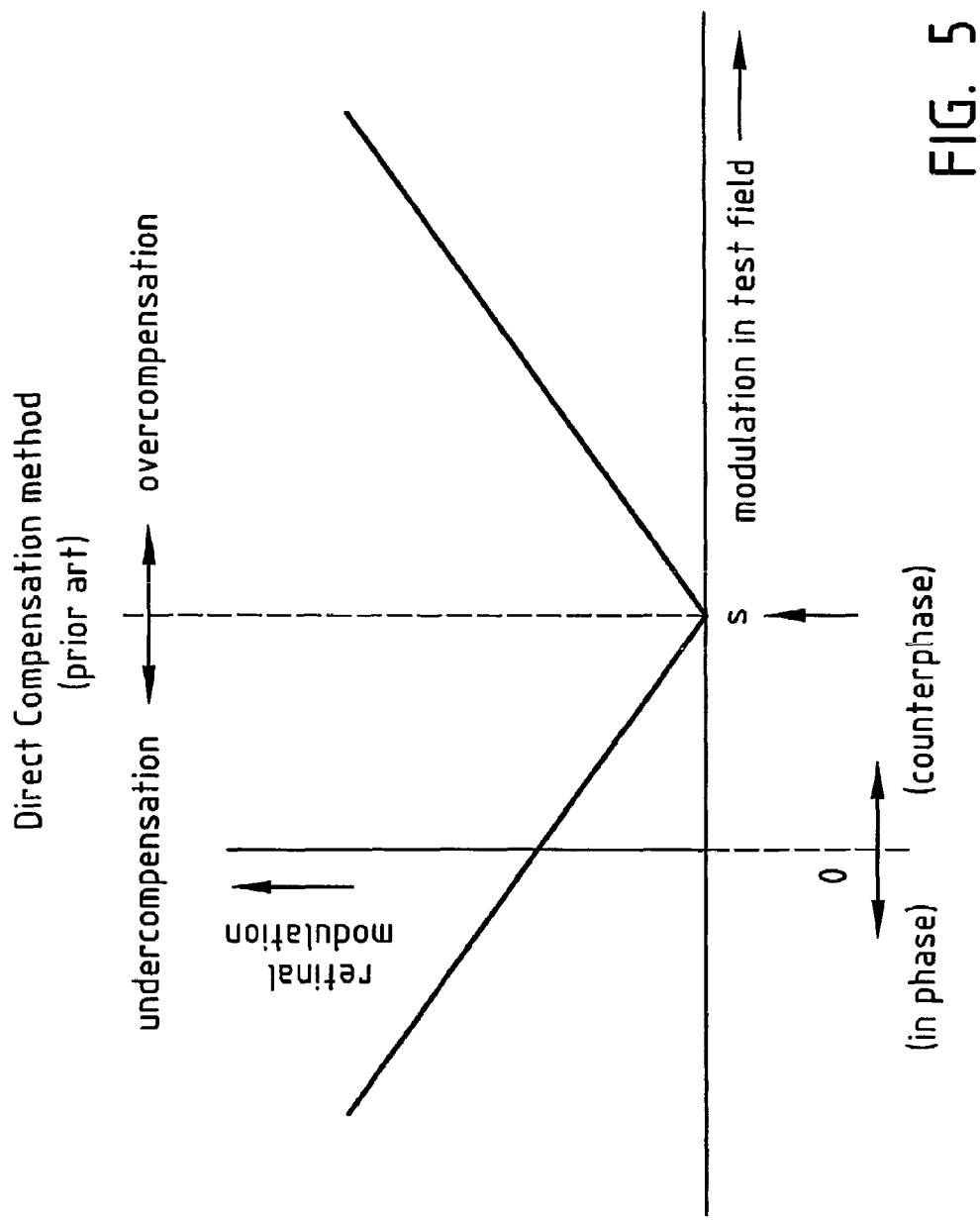
FIG. 5 shows a graph of the retinal flicker intensity as function of the flicker intensity of the test field in case of the prior direct compensation method.
Figure 6A:
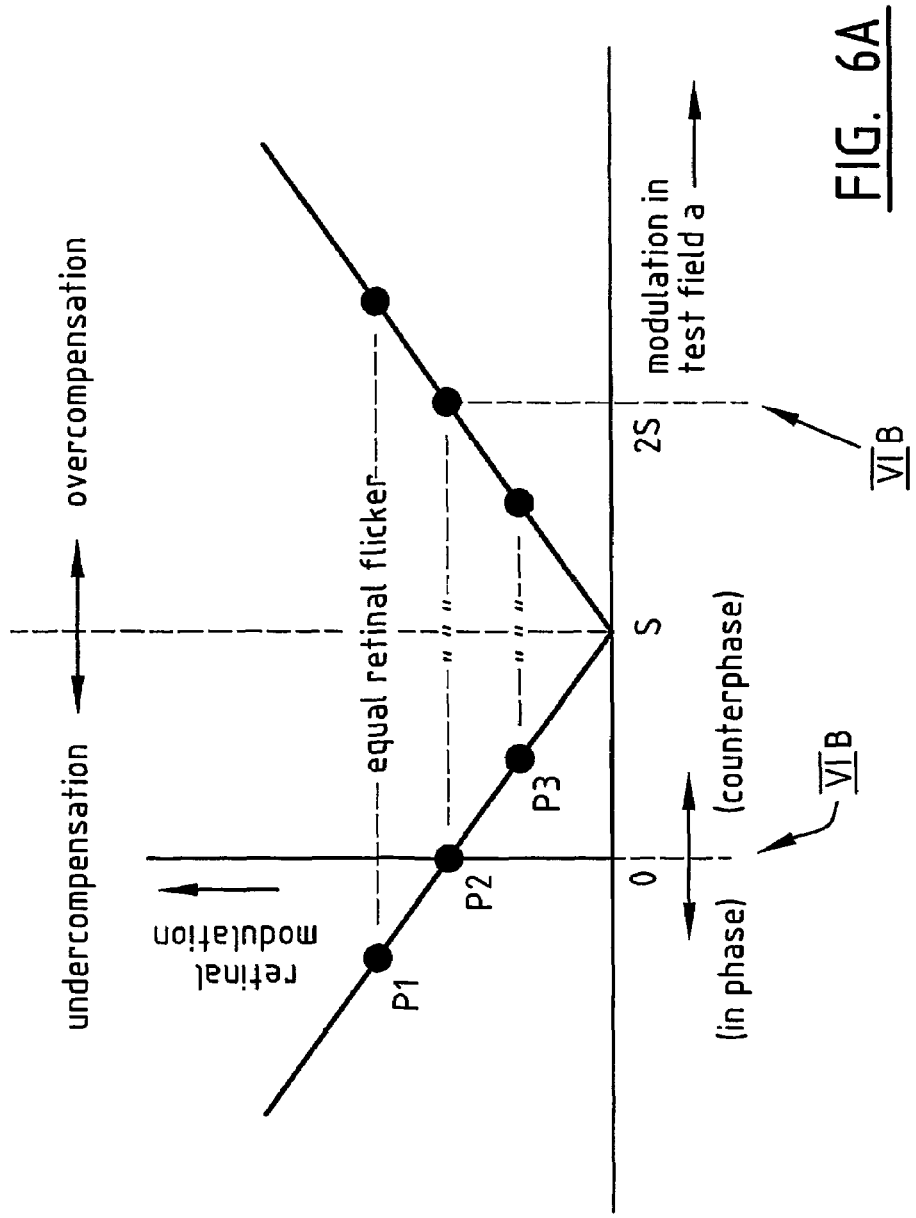
FIG. 6A shows a graph of the retinal flicker intensity as function of the flicker intensity of the test field in case of the flicker matching method according to the present invention wherein three different levels of over-/under compensation are used.
Figure 6B:
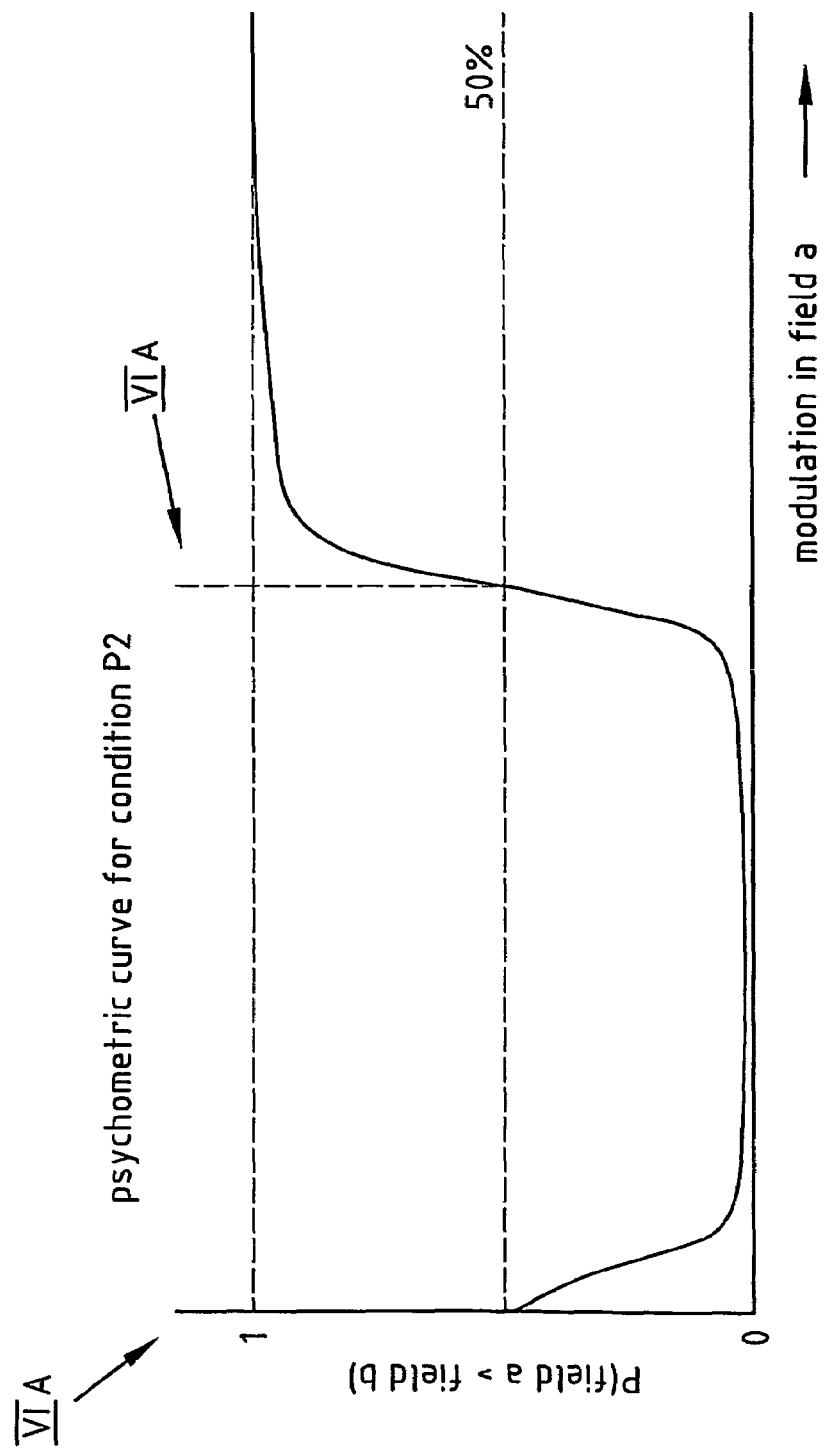
FIG. 6B shows the psychometric function for the type of judgement as illustrated in FIG. 6A wherein under compensation condition P2 of FIG. 6A is used, i.e. no compensation.

In FIGS. 5, 6a, and 6b along the horizontal axes the compensation luminance in the test field is varied and expressed according to this rule as s. In the known direct compensation method, as is shown in FIG. 5, the subject adapts the value of s by operating a switch and by determining the value of s at which the perceived retinal flicker intensity is a minimum. In the present flicker matching method the value of 2s is determined, as the sum of s in two half fields, as will be explained hereafter.

In the above-described embodiment use is made of an analogue cathode ray tube (CRT) display device. In another preferred embodiment the display device is of the Digital Light Processing (DLP™) type, wherein digital images can be provided. A suitable DLP device is for example the Texas Instruments, type DMD 0.7 XGA DDR). In this type of display device use is made of a projection lamp and a digital micro mirror device (DMD) consisting of an array of thousands small-sized mirrors, each mounted on a hinge structure so that it can be individually tilted back and forth. The DLP type display device processes the digital input signal and tilts the mirrors to directly generate a digital image. One of the advantages of a DLP is that no calibration step is needed. Furthermore, the DLP device is more compact than a computer monitor and is able to provide higher luminances.

Once the measuring device 1 is calibrated, the measurement of the stray light parameter of an eye of the subject can commence. For the comparisons to be made, the test field is subdivided into two or more spatially separated sections (simultaneous comparisons) and/or into two or more temporally separated sections (sequential comparisons). For simplicity the test field sections are hereafter referred to as test fields. The test fields are overcompensated or under compensated, giving relatively large modulation depths, such that the resulting flickering is relatively easily perceived, even for untrained subjects.

In the following, the invention will be described for the simple case of a comparison of two test field sections or test fields only, but multiple test fields are also included in the invention. In the case of one overcompensated and the other under compensated test field and if these test fields have equal true retinal flicker amplitude (including the scattered light), the stray light of the eye is given by: $s = \theta^2 (L_{uc} - L_{oc})/(2E_{g1})$, where $L_{uc}$ is the (flicker) luminance given to the undercompensated field and $L_{oc}$ is the (flicker) luminance given to the overcompensated field ($L_{uc} < L_{oc}$). These luminances have a positive sign when in counterphase with the glare source, and a negative sign when in phase with the glare source.

FIG. 3 shows a preferred embodiment of a circle symmetric stimulus configuration displayed on the display device. Shown is a stimulus field layout comprising an outer ring 12 simulating a flickering stray light source. In the centre of the ring 12 is arranged a test circle 13 surrounded by a ring 14. This is a high intensity ring shaped light source surrounding the test circle in order to isolate the test circle from other parts of the display area and to suppress flicker influences from the surround area. The area abutting the stray light source ring 12 on the inside is called the inner periphery or surroundings 19 of the ring 12, while the area outside the ring 12 is called the outer periphery or surroundings 18. Steady light in the surroundings (areas 18 and 19) is applied to suppress flicker stimulation in those areas. The intensity is preferably of the same order as that of the straylight annulus.

The test circle 13 is in the present embodiment subdivided in a left half circle or left test field 15 and a right half circle or right test field 16. The subject is presented simultaneously with an undercompensated test field and an overcompensated test field. The undercompensated test field can be either the left test field 15 or the right test field 16. In case the undercompensated field is the left test field 15, the right test field 16 is overcompensated, while if the undercompensated test field is the right test field 16, the left test field 16 is overcompensated.

In a further preferred embodiment the undercompensated and overcompensated test fields are interchanged arbitrarily during the presentation of consecutive stimuli, i.e. the undercompensated field and the overcompensated field may be shown at random in the left test field 15 or in the right test field 16. This will further reduce the risk that a test person's preference for either the left or the right test field will unintentionally influence the outcome of the measurements. Consequently, when in the figures and description the test fields are referred to as left test field 15 and right test field 16, in fact reference is made to a first test field (a) and a second test field (b), which may at random be the right and left test field.

The stimuli are presented with a frequency of preferably 8-10 Hz (since people appear to be relatively sensitive to flicker at this frequency) and with a finite duration, typically between 0.5 and 5 seconds, preferably about 1 second. A random or pseudo random algorithm determines which side of the field represents the overcompensated test field and which side of the field represents the undercompensated test field. Stimuli are presented starting at a predetermined overcompensation, typically an overcompensation of $\log(s) = 2.5$. Subsequent trials have a lower overcompensation, with predefined decrements, for example decrements of 0.3 log(s) units at first and 0.1 log units later.

During or after presentation of the stimuli the subject has to respond which of the two test fields 15,16 flickers or flickered most by pressing either of the response buttons 9,10 of the first input terminal 3. A choice for the overcompensated field is recorded as 1 and a choice for the undercompensated field as 0. This is a measurement set-up according to the well-known two-alternative forced choice (2AFC).

A maximum likelihood algorithm is used to detect a reversal, i.e. when there is statistical significance that the subject has reached the rapid transition located at twice the s value of the eye, and the decrement in overcompensation stops. At this time, there is an initial estimate of the s value of the eye. Based on this value the measurement is refined by presenting stimuli near the reversal point.

The number of stimuli presented in this second phase of the test, as well as the width of the interval tested, can be chosen prior to the test. In the second phase the order in which the stimuli are presented is chosen randomly, in accordance with the method of constant stimuli. Obviously, measurement accuracy increases with the number of trials in the second phase. After the presentation of the trials in the second phase, all data from the test are used in a maximum likelihood fit. This fit gives the final estimate of the reversal point. Additionally, the maximum likelihood procedure gives an estimate of the accuracy of the obtained s value. This estimate of the accuracy is reported to the operator as feedback, such that, in case a subject did not completely understand the visual task, the test can be better explained. All relevant data, such as subject responses, date/time, the time that the system has been on, and the calibration data are automatically stored on the storage means 17 of the computer 1.

In one preferred embodiment the undercompensated test field is kept at zero compensation, while the overcompensated test field has a variable overcompensation. The annulus shaped stray light source flickers with maximum achievable modulation depth. This measurement set-up is shown at P2 in FIG. 6A. FIG. 6A shows the retinal flicker in the eye during a flicker comparison measurement. The markers show equal retinal flicker for this level of over-/under compensation. Points of equal retinal flicker are indicated with arrows. The point of symmetry -where the V-shape has its minimum, in this case zero, value-corresponds to the stray light s value of the eye being measured.

In the present embodiment the left test field 15, or, for the reasons stated earlier, rather a test field (a), is undercompensated with zero compensation and therefore has a retinal flicker intensity $I_1$. In the right test field 16, or rather the test field (b), the compensation is varied. The point at which the retinal flicker intensity of the right test field 16 equals the retinal flicker intensity $I_1$ of the non-compensated left test field 15 defines twice the value of the stray light parameter s, as can be clearly seen in FIG. 6a.

Above embodiments have been discussed wherein the test field (b) is not compensated, which in fact is only one form of undercompensation. Other forms are more or less undercompensation. The general rule for interpretation of the point along the s scale where the two half fields appear equal is that s for the respective subject equals half the sum of s in the two half fields. This can be understood from FIG. 6a. In case of non-compensation in half field b, $s_b$=0, and at the point of equality $s_a$=2s.

In other embodiments the left test field 15 may be further undercompensated, for example as is shown at P1 in case of in-phase modulation in half field (b), or less undercompensated, for example as is shown at P3 in case of a 0.5 s counterphase modulation in half field (b). Then the values of equal retinal flicker may be higher or lower than the intensity $I_1$, as is shown in FIG. 6A. The value of the stray light parameter s may be derived from the V-shaped curve in a similar way by determining the point of symmetry of the curve. This point will give the value of the stray light parameter s.

The perception of retinal flicker difference is governed by so-called psychometric functions. A psychometric function describes the chance of a certain response of the subject (e.g. "the left half of the test field flickers stronger than the right half") to a presented stimulus. In case of two (independent) compensation stimuli the psychometric space span is 2-dimensional. However, in one preferred embodiment one of the stimuli is constant and each pair of stimuli can be treated as one stimulus value, by considering only the variable modulation depth.

FIG. 6b shows an example of this psychometric function, containing the probability of the response that "field a flickers stronger than field b" for the case that no compensation is present in field (b). For more precise applications or more complex embodiments, more complicated psychophysical functions apply. The psychometric function results in a fit giving in this instance a final estimate of a reversal point that is located at two times the s of the eye, as can clearly be derived from FIGS. 6a and 6b.

This psychometric curve has some similarities and some peculiar differences with psychometric curves known from other visual tests, e.g. the curve corresponding to a yes-no task in visual field testing. The curve has a high value for large overcompensation, and has a rapid transition to a low value at an overcompensation of twice the s of the eye. This rapid transition is used to measure the amount of light scatter in an eye. In case the intended overcompensated field is, in fact, (severely) undercompensated, the curve shows a transition to high values again. This shape of the psychometric curve is clearly shown in FIG. 6b.

Figure 7:
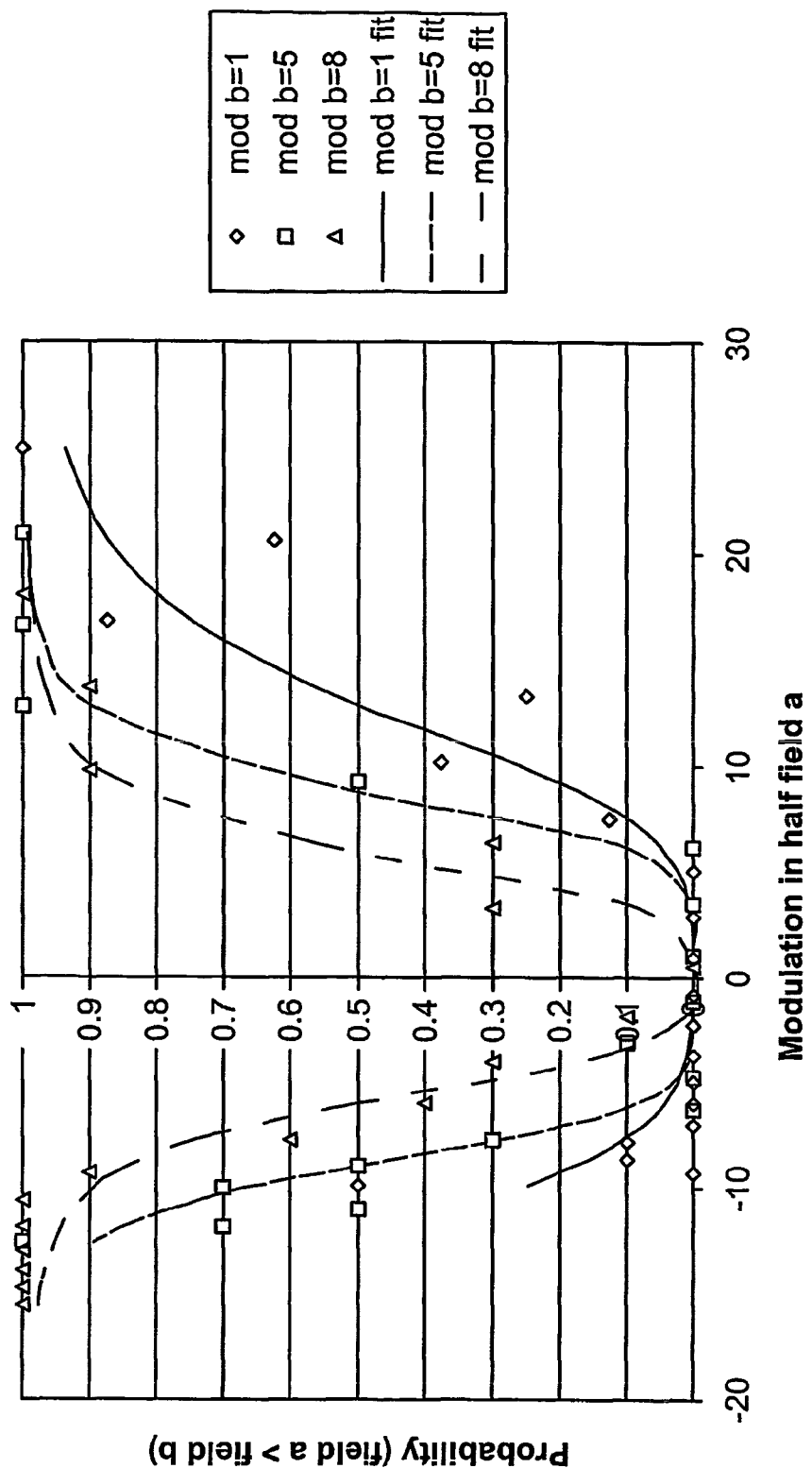
FIG. 7 shows experimental curves when different amounts of compensation (s=1, s=5 and s=8) were given in a half field (half field b).

In FIG. 7 examples are shown of experimental curves when different amounts of compensation was given in half field (b), for a subject with s=14. The value s=14 is plotted as the origin (modulation=0). The (fixed) values for $s_b$ were 8, 5 and 1. It can be seen that the modulation needed for equality (50% chance a>b) are about 6 (+14), 9 (+14) and 13 (+14) respectively, corresponding to the above-mentioned rule that the sum of the two compensations equals s. This figure shows that the psychometric curves creep closer to the point of "direct compensation" (the origin, were s=14 and retinal modulation is zero). At the same time the slopes of the psychometric curves get steeper. Both effects ensure that higher measurement accuracy is obtained.

In another preferred embodiment a staircase procedure instead of the two phase measurement technique described above can be used to determine which stimulus level to present. Preferably this staircase procedure has an initial step-size of 0.3 log(s) units, and gets a smaller stepsize after each reversal. The algorithm that determines the next stimulus level is described in literature as the Accelerated Stochastic Approximation" (see for example the article "Minireview Adaptive Psychological Procedures" by Bernhard Treutwein, Vision Res., Vol. 35, No. 17 pages 2503-2522, 1995).

In a further preferred embodiment an offset in either the under compensation or overcompensation test field, which depends on the amount of under- and overcompensation for that particular stimulus, is added in order to ensure that the subjects gets no clues to detect a difference between the two test fields, other than a difference in the amount of flicker. In other words, the parameters in the two test fields, in particular the average luminance of the test fields, are kept to be the same as much as possible. By adding an offset in either the under compensation or overcompensation test field, which depends on the amount of under- and overcompensation for that particular stimulus, the average luminance of the test fields changes during a test, but is always the same for the under compensation and overcompensation fields presented at the same time. In another preferred embodiment also the change in average luminance during a test is eliminated by adding suitable amount of offset.

In fact, the precise strategy for the comparisons, the way in which they lead to estimates of retinal stray light, and the choice of the over- and/or undercompensations may vary, depending on the application. But for some applications preferred embodiments will be described below.

The actual choice of compensations can be made according to various well known psychophysical procedures, such as, but not limited to:

Method of adjustment. According to this method the subject has control of the stimulus intensity. The subject must find the equal flicker point by turning a knob or pushing buttons or keys. An advantage of the method of adjustment is that it is relatively fast.

Method of constant stimuli. According to this method the order of presentation of the stimuli in any trial is random, so that the subject has no way of anticipating the intensity of the stimulus, It is not the stimuli that are constant, it is what the subject expects that does not change from trial to trial. The result of this method is a psychometric function, from which the stray light parameter can be derived.

Fixed step staircase (presented stimulus depends on previous answer, but step size is constant)

Stochastic approximation (presented stimulus depends on previous answer, step size becomes smaller with each stimulus)

Accelerated stochastic approximation (same as stochastic approximation, but the step size changes only at reversals)

Maximum likelihood procedures (stimulus depends on all previous answers)

In another preferred embodiment (also known as the "dark" version of the method and device according to the invention) the amounts of overcompensation and undercompensation in the respective test fields are kept at a constant level, while the amount of perceived flicker is varied by altering the intensity of the flickering stray light source. The surroundings of the stray light source (referred to as periphery) have a luminance equal to the level of the stray light source. In a preferred version of this embodiment the test starts at low luminance levels (stray light source as well as periphery) and gradually becomes brighter, making the comparison task more difficult. This would be in accordance with real life situations, where a brighter stray light source will make detection of a low level target object more difficult.

In another preferred embodiment the measurement is started with a flicker comparison task, as in the previous embodiments, but without a flickering stray light source. With this so-called flicker detection threshold measurement it is possible to determine the subject's ability to detect flicker (flicker sensitivity). The second phase of the test is similar to the second phase in the "dark version" embodiment. This part is used to find the reversal point, as described in the light version embodiment. The third phase of the test is the second phase of the light version embodiment, which entails presentation of stimuli around the reversal point, according to the method of constant stimuli, with a stray light source flickering at maximum intensity.

In another preferred embodiment the test fields and/or the stray light source and/or the periphery have different colours, especially the colours blue, green and red. The colours may be provided in any combination (e.g. green stray light source, green test fields, white periphery). In this way the stray light parameter in dependence of the respective wavelength of the compensation light and/or stray light can be determined. The stray light parameter in dependence of the wavelength may give useful information on the functioning of the eye.

Different parts of the eye that contribute to stray light have different spectral dependencies. Hence, comparison of the straylight result for different colours provides information about the relative weights of different parts of the eye for their contribution to the total stray light. This can be of relevance for clinical diagnosis, or for judging more precisely what stray light hindrance to expect in particular situations. For example, a low sun is reddish, so its hindrance depends more on straylight in the reddish end of the spectrum. The most straightforward way of measurement would be to use complete red, green or blue straylight meters. This can be realised e.g. by having the same computer monitor based instrument, but having either the red, green or blue phosphor solely used. However, combinations of colours may be of interest to establish directly the ratios between them. E.g. if the red phosphor of the stray light annulus is modulated in counterphase to the green phosphor within that same annulus, the relative balance between the two modulations needed to extinguish the flicker perceived in the centre directly gives the ratio in stray light parameter between the two colours.

In the above-described embodiments the subject is always forced to make a choice, i.e. he/she must choose which of the test fields is perceived as having the highest (or lowest) retinal flicker intensity (forced choice method). In another embodiment input terminal 3 is provided with a third response button. By pressing this response button the subject may indicate that the result of the comparison was undecided (no-choice possibility).

In another preferred embodiment the angle theta of the stray light source may be changed, for example from 10 degrees to 3 degrees. Especially for driver testing purposes a theta of 3 degrees appears to be most relevant. Different parts of the eye that contribute to stray light have different angular dependencies. Hence, a comparison of the strayliqht result for different angles provides information about the relative weights of different parts of the eye for their contribution to the total stray light. This can be of relevance for clinical diagnosis or for judging more precisely what stray light hindrance to expect in particular situations. For example, an oncoming car is localized typically at 3 degrees, so its hindrance depends more on straylight at 3 degrees. As another example, the angular dependence of the straylight contribution from the transparency of the eye wall (component iris/sclera in FIG. 1) is know to be isotropic as opposed to the other components. So a measurement of the angular dependence can be used to estimate de relative contribution of such component. The most straight forward way of measurement would be to use a straylight annulus located at angle of interest. In a computer monitor based instrument the angle of the annulus can simply be varied, and the straylight parameter measured for different angles separately. However, combinations of angles may be of interest to establish directly the ratios between them. E.g. if an annulus at 3 degrees is modulated in counterphase to an annulus at 10 degrees at the same time on the same monitor, the relative balance between the two modulations needed to extinguish the flicker perceived in the centre, directly gives the ratio in stray light parameter between the two angles.

In the above a flicker frequency of 8-Hz was mentioned since people are most sensitive to flicker at this frequency. However, in another preferred embodiment different flicker frequencies are used. Depending on the use, especially with respect to population subgroup, different flicker frequencies may be best suited for accuracy. It is known that with retinal illness and age flicker perception changes. Also, when using other parameters such as colour, angle, annular width, etc., the frequency for best performance changes.

Instead of the square wave flicker signal described so far, the shape of the flicker signal may also be changed. For example a sinusoidal or a triangular wave shape may be beneficial for certain specific applications as just explained, since these waveforms comprise different frequencies.

In another preferred embodiment the stimuli are separated temporally as opposed to the embodiments employing a spatial separation described so far. In this embodiment the overcompensation and under compensation test fields are presented one after the other at the same complete circular test field spot, instead of presentation in two half circular spots at the same time. Flicker sensitivity depends on size of test field. With two half fields, sensitivity is lost as compared to one full circular field. Depending on the application the benefit of simultaneous comparison may be out-weighted by this effect.

Figure 8:
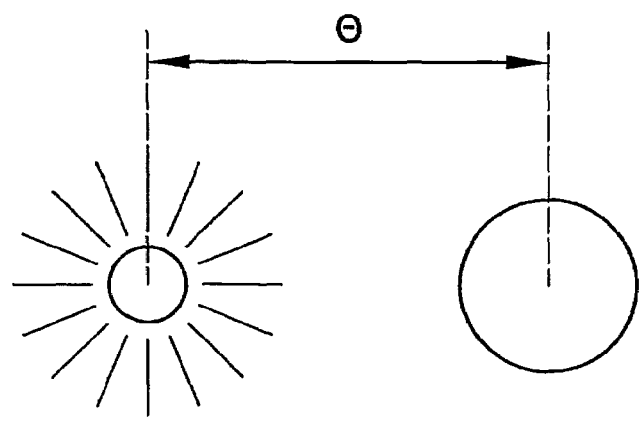
FIG. 8 shows a front view of the geometrical arrangement of a further preferred embodiment of the stimulus field layout represented on the display device.

The geometry of the stray light source may be adapted depending on the specific purpose of the stray light measurement. FIG. 8 shows another preferred embodiment wherein one or more bright point sources are used instead of a ring-shaped source. This may correspond better to specific hindrance situations, such as during driving at night. Also, the stray light annulus may be changed in shape, especially decreased in width. This is of interest if better angular resolution is needed. In the present embodiments, the outer radius is twice the inner radius of the annulus. An example of such application is the measurement of the so-called lenticular halo. This phenomenon, relevant as a pre-phase of cataract, is characterised by a sharp peak in straylight at a few degrees of visual angle. Also different types of stray light sources may be used, such as for example LED's, and/or other types of compensation light sources may be used.

In a further preferred embodiment the light from the stray light source is aimed at the blind spot in the eye. The stray light is in this case not or at least less perceived and less disturbing for the test person and therefore for the outcome of the measurements.

The size of the test field itself may influence the outcome of the determination of the stray light parameter. The size of the test field influences sensitivity as well as angular resolution. With increasing size, sensitivity improves but resolution decreases. Depending on the application an optimal balance between these two effects can be obtained.

So far the two-alternative forced choice (2AFC) measurement has been described. However, the number of alternatives may be increased to three, four or more (3AFC, 4AFC etc). In general, the more alternative choices there are, the lower the expected score for guessing, but also the greater the chance of the subject becoming confused or missing the stimulus because it is difficult to attend to so many test fields.

Therefore in another preferred embodiment three or more test fields are presented on the display device in order to present three or more alternative choices to the subject for spatially as well as temporally separated stimuli. The psychometric approach determines speed and accuracy of measurement. Speed of measurement may be increased by multiple simultaneous comparisons. But this task will be more demanding on the subjects. Consequently, this embodiment will be used for specific subject groups only.

In another preferred embodiment the duration of the stimulus is varied, for example from the preferred duration of about 1 second to for example 10 seconds or more. The response time within which the subject has to answer may be varied as well. This variation can be used to optimise subject performance. Some subjects may improve their performance when presentation time is lengthened whereas others may loose on their performance. Individual adaptation of presentation and response times may dynamically be accomplished, guided by the actually measured performance of the subject.

The image presented in between measurements may have the same average luminance as the luminance presented during the tests. Alternatively the image may be black or may have a maximum intensity. This determines the pre-adaptation state for the presentation. This can be optimised for best performance during the presentation.

A non-uniform compensation field can be used to more accurately mimic the straylight distribution in the test field. Since straylight depends strongly on angle, the straylight distribution in the test field also shows some non-uniformity, depending on geometry of the straylight source.

The present invention also contemplates all combinations of the above-described preferred embodiments. For example combinations of either the light or dark version embodiments with all types of different psychophysical measurement techniques (e.g.: method of adjustment, method of constant stimuli, fixed step staircase, stochastic approximation, accelerated stochastic approximation, and maximum likelihood procedures) are feasible. The invention also includes all of the above with different variations of over- and undercompensation. For instance:

constant undercompensated test field part and variable overcompensation test field part, as for example described in the first embodiment of a zero undercompensated test field;

constant difference between undercompensated and overcompensated test field and variable sum of these two in case if the "light version" or variable stray light source in case of the "dark version".

The present invention is not limited to the above-described preferred embodiments thereof; the rights sought are defined by the following claims, within the scope of which many modifications can be envisaged.

The invention claimed is:

1. Method of measuring the retinal stray light in the eye of a subject, comprising:

presenting to the subject a flickering stray light from a stray light source positioned at a predefined angular distance from a test area, a part of the flickering stray light being imaged on the retina at a location corresponding to the location of the test area;

presenting to the subject compensation light from a compensation light source arranged at a position in the test area, the parameters of the compensation light being set so as to undercompensate said part of the flickering stray light being imaged on the retina at the location corresponding to the location of the test area;

presenting to the subject compensation light from a compensation light source arranged at a position in the test area, the parameters of the compensation light being set so as to overcompensate said part of the flickering light being imaged on the retina at the location corresponding to the location of the test area;

receiving an input signal representative of the result of a comparison between the resulting retinal light flickering as perceived by the subject for the undercompensated test area and the resulting retinal flicker intensity for the overcompensated test area;

varying the value(s) of one or more of said parameters defining one or more of the stray light source light and the compensation light source light;

repeating the above steps for different parameter values;

determining, using the received input signals and the corresponding parameter values of the stray light source and the compensation light sources, those parameter values wherein the perceived retinal light intensities of the undercompensated and overcompensated test area are substantially equal; and calculating from the determined parameter values a stray light parameter representative of the retinal stray light induced by the stray light source.

2. Method according to claim 1, wherein in the first step of presenting to the subject compensation light from a compensation light source, the compensation light is in phase or in counterphase with the stray light source and is provided with a modulation depth, including a zero modulation depth, so as to undercompensate said part of the flickering stray light being imaged on the retina at the location corresponding to the location of the test area;

wherein in the second step of presenting to the subject compensation light from a compensation light source, the compensation light flickers with a modulation depth so as to eventually overcompensate said part of the flickering light being imaged on the retina at the location corresponding to the location of the test area;

wherein, using the results of the repetitions and based on the input signals, the modulation depths are determined of the stray light source, the undercompensated test area and the overcompensated test area wherein the perceived retinal light intensities of the undercompensated and overcompensated test area are substantially equal; and wherein from the determined modulation depths a stray light parameter representative of the retinal stray light is determined.

3. Method according to claim 2, wherein the parameter varied is the modulation depth of the light from the stray light source.

4. Method according to claim 2, wherein the parameter varied is the modulation depth of the compensation light for at least one of the undercompensated and overcompensated test areas.

5. Method according to claim 4, wherein the periphery light from the surroundings of the stray light source has a luminance substantially equal to the luminance of the stray light source.

6. Method according to claim 1, wherein the first and second compensation lights are presented consecutively in time.

7. Method according to claim 1, wherein the first and second compensation lights are presented simultaneously.

8. Method according claim 7, wherein the test area comprises at least a first and a second test field being spatially separated and wherein a first compensation light source is arranged at the position of the first test field and a second compensation light source is arranged at the position of the second test field.

9. Method according to claim 8, comprising after having received the input signal:

varying the summed modulation depth of the compensation light of the undercompensated test field and the overcompensated test field, while keeping a constant difference between the modulation depths of the undercompensated and overcompensated test fields; and repeating the presenting steps and receiving step using the varied summed modulation depth until the modulation depth is determined wherein the perceived retinal light intensities of the undercompensated and overcompensated test area are substantially equal.

10. Method according to claim 1, wherein an offset in either the undercompensation or overcompensation test field is added, the offset depending on the amount of under- and overcompensation for a particular stimulus.

11. Method according to claim 10, wherein the average luminance of the undercompensated test field is set so as to correspond with the average luminance of the overcompensated test field presented at the same time.

12. Method according to claim 1, comprising the step of presenting compensation light in one or more of the test fields without presenting light from the stray light source so as to determine the detection threshold of flickering light of the subject.

13. Method according to claim 12, wherein determining the flickering light detection threshold of the subject comprises presenting compensation light of varying modulation depth differences in the test fields without presenting light from the stray light source; and determining the value of the minimum modulation depth difference that can be sensed by the subject.

14. Method according to claim 1, comprising:

determining a first estimate of the stray light parameter by using the method of varying the light from the stray light source; and determining a second estimate of the stray light parameter by using the method of varying the modulation depth of at least one of the test fields, wherein the modulation depths presented are based on the first estimate of the stray light parameter.

15. Method according to claim 4, wherein the stray light source presents flickering light at a maximum intensity.

16. Method according to claim 1, wherein the stray light source has an annular shape.

17. Method according to claim 15, wherein the stray light source comprises one or more point sources.

18. Method according to claim 16, wherein the test area has a circular shape, preferably divided in two equal parts.

19. Method according to claim 18, wherein the test area is situated in the centre of the annulus and the straylight parameter s is defined as:

$$s = L_{eq}/(0.0044 \cdot {}^{10}\log(\theta_2/\theta_1) \cdot c)$$

wherein $L_{eq}$ is the compensation luminance needed in the test field and c is the luminance of an annular stray light source with inner angular radius of $\theta_1$ and outer angular radius of $\theta_2$.

20. Method according to claim 1, wherein a high intensity ring shaped light source surrounding the test area is provided for isolating the test area from the surroundings.

21. Method according to claim 1, wherein the stray light source is surrounded by light filled areas, such as an outer area and an inner area, to suppress flicker in those areas.

22. Method according to claim 1, wherein the test fields and/or the stray light source are presented with different colours in order to determine the stray light parameter in dependence of the wavelength of the stray light.

23. Method according to claim 1, wherein the retinal stray light in both eyes of a subject is determined simultaneously.

24. Method according to claim 1, wherein between consecutive presentations of stray light and compensation light an image is presented for pre-adaptation.

25. Method according to claim 24, the image having an average luminance corresponding to that of the average luminance during said presentations.

26. Method according to claim 1, further comprising the step of storing relevant data, such as subject input, date and time.

27. Method according to claim 1, wherein the test area is provided with blurred edges.

28. Method according to claim 1, wherein variable offsets in the test fields of the test are provided.

29. Method according to claim 1, wherein the undercompensation and overcompensation of the test fields are modulated spatially.

30. Method according to claim 29, wherein the spatial modulation is about 2 to about 4 Cycl/deg.

31. Method according to claim 1, wherein the light from the stray light source is aimed at a blind spot in the eye.

32. Method according to claim 1, wherein the duration of the presentation of the light from the stray light source and at least one compensation light source is varied.

33. Method according to claim 1, wherein the response time is varied within which subject has to provide the result of his comparison.

34. Method according to claim 1, wherein the angle (θ) of the stray light source is varied.

35. Method according to claim 1, wherein the flicker frequency of the compensation light source and/or of the stray light source is varied.

36. Method according to claim 1, wherein the test field has a non-uniform test area.

* * * * *